(12) United States Patent
De Groot et al.

(10) Patent No.: US 11,998,347 B2
(45) Date of Patent: Jun. 4, 2024

(54) SLEEP APNEA DETECTION SYSTEM AND METHOD

(71) Applicant: KONINKLIJKE PHILIPS N.V., Eindhoven (NL)

(72) Inventors: Koen Theo Johan De Groot, Sevenum (NL); Pedro Miguel Fonseca, Borgerhout (BE); Jenny Margarito, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 438 days.

(21) Appl. No.: 16/977,595

(22) PCT Filed: Mar. 6, 2019

(86) PCT No.: PCT/EP2019/055557
§ 371 (c)(1),
(2) Date: Sep. 2, 2020

(87) PCT Pub. No.: WO2019/170734
PCT Pub. Date: Sep. 12, 2019

(65) Prior Publication Data
US 2020/0405222 A1  Dec. 31, 2020

(30) Foreign Application Priority Data
Mar. 7, 2018 (EP) .................................. 18160523

(51) Int. Cl.
*A61B 5/00* (2006.01)
*A61B 5/024* (2006.01)
(Continued)

(52) U.S. Cl.
CPC ........ *A61B 5/4818* (2013.01); *A61B 5/02405* (2013.01); *A61B 5/02416* (2013.01);
(Continued)

(58) Field of Classification Search
CPC .............. A61B 5/4818; A61B 5/02405; A61B 5/02416; A61B 5/4812; A61B 5/681; A61B 5/7267; A61B 5/7264
See application file for complete search history.

(56) References Cited

U.S. PATENT DOCUMENTS

2005/0054940 A1* 3/2005 Almen ................. A61B 5/4809
600/509
2005/0177051 A1* 8/2005 Almen ............... A61B 5/02438
600/509

(Continued)

FOREIGN PATENT DOCUMENTS

TW        201922168 A  *  6/2019  ........... A61B 5/0205

OTHER PUBLICATIONS

International Search Report and Written Opinion of PCT/EP2019/055557, dated May 27, 2019.
(Continued)

*Primary Examiner* — Rex R Holmes
*Assistant Examiner* — Sana Sahand

(57) ABSTRACT

A method and system for detecting sleep apnea involves determining the sleep stage, and detecting an apnea event based on a physiological sensor signal using selection of a detection algorithm which is dependent on the determined sleep stage. By taking account of the sleep stage when performing an automated apnea detection process, the accuracy of the apnea detection is improved.

9 Claims, 7 Drawing Sheets

(52) U.S. Cl.
CPC ............ *A61B 5/4812* (2013.01); *A61B 5/681* (2013.01); *A61B 5/7267* (2013.01)

(56) References Cited

U.S. PATENT DOCUMENTS

| | | | |
|---|---|---|---|
| 2006/0235315 A1* | 10/2006 | Akselrod | A61B 5/02405 600/509 |
| 2008/0033304 A1 | 2/2008 | Dalal | |
| 2014/0200474 A1* | 7/2014 | Selvaraj | A61B 5/0806 600/529 |
| 2015/0119741 A1* | 4/2015 | Zigel | A61B 5/7275 600/529 |
| 2015/0164238 A1 | 6/2015 | Benson | |
| 2017/0055898 A1 | 3/2017 | Bandyopadhyay | |
| 2017/0215808 A1 | 8/2017 | Shimol | |
| 2018/0106897 A1* | 4/2018 | Shouldice | A61B 5/0507 |
| 2019/0150772 A1* | 5/2019 | Haraikawa | A61B 5/7267 |

OTHER PUBLICATIONS

Berry, Richard B. et al "Rules for Scoring Respiratory Events in Sleep: Update of the 2007 AASM Manual for the Scoring of Sleep and Associated Events: Deliberations of the Sleep Apnea Definitions Task Force of the American Academy of Sleep Medicine" Journal of Clinical Sleep Medicine: vol. 8, No. 5, pp. 597-619, 2012.

Fonseca, P. et al "Sleep Stage Classification with ECG and Respiratory Effort", Institute of Physics and Engineering in Medicine, Physiological Measurement, vol. 36, pp. 2027-2040, 2015.

Kesper, K. et al "ECG Signal Analysis for the Assessment of Sleep-Disordered Breathing and Sleep Pattern", Medical & Biological Engineering & Computing, vol. 50, No. 2, pp. 135-144, 2011.

Fontenla-Romero, Oscar "A new method for sleep apnea classification using wavelets and feedforward neural networks" Artificial Intelligence in Medicine, vol. 34, pp. 65-76, 2005.

Lee, Won et al "Epidemiology of Obstructive Sleep Apnea: A Population-Based Perspective", Expert Review of Respiratory Medicine, vol. 2, No. 3, pp. 349-364, 2008.

Khandoker, Ahsan H et al "Support Vector Machines for Automated Recognition of Obstructive Sleep Apnea Syndrome from ECG Recordings", IEEE Transactions on Information Technology in Biomedicine, vol. 13, No. 1, Jan. 2009.

Hassan, Ahmaf Rashik, "Computer-aided obstructive sleep apnea screening from single-lead electrocardiogram using statistical and spectral features and bootstrap aggregating", Biocybernetics and Biomedical Engineering, vol. 36, pp. 256-266, 2016.

Penzel, T. et al."The Apnea-ECG Database", Computers in Cardiology, vol. 27, pp. 255-258, 2000.

Chai-Coetzer, Ching Li et al "The Debate Should Now Be Over. Simplified Cardiorespiratory Sleep Tests are a Reliable, Cost-saving Option for Diagnosing Obstructive Sleep Apnea", American Journal of Respiratory and Critical Care Medicine, vol. 196, No. 9, pp. 1096-1097, 2017.

Stein, Phyllis K. et al "Heart Rate Variability, Sleep and Sleep Disorders", Sleep Medicine Reviews, vol. 16, Issue 1, pp. 47-66, Feb. 2012.

Fonseca, Pedro et al "Validation of Photoplethysmography-Based Sleep Staging Compared With Polysomnography in Healthy Middle Aged Adults", Sleep, vol. 40, Issue 7, 2017.

Isa et al., "Sleep Apnea Detectionfrom ECG Signal: Analysis on Optimal Features, Principal Components, and Nonlinearity" 2011 5th, International Conference onBioinformatics and Biomedical Engineering, May 12, 2011.

Almazaydeh et al., "Detection of obstructive sleep apnea through ECG signal features", 2012IEEE International Conference on Electro/Information Technology, May 8, 2012.

Sulistyo et al., "Sleep Apnealdentification using HRV Features of ECG Signals" International Journal of Electrical and Computer Engineering, vol. 8, No. 5, Oct. 31, 208, pp. 3940-3948.

\* cited by examiner

SLEEP APNEA DETECTION SYSTEM AND METHOD

CROSS-REFERENCE TO PRIOR APPLICATIONS

This application is the U.S. National Phase application under 35 U.S.C. § 371 of International Application Serial No. PCT/EP2019/055557, filed on Mar. 6, 2019, which claims the benefit of European Patent Application Serial No. 18160523.9, filed on Mar. 7, 2018. These applications are hereby incorporated by reference herein.

FIELD OF THE INVENTION

This invention relates to the detection of sleep apnea, where apnea is used as a general term to include obstructive sleep apnea, central sleep apnea but also hypopnea episodes.

BACKGROUND OF THE INVENTION

Sleep apnea is a general term used to designate two types of sleep breathing disorders, namely obstructive sleep apnea (OSA) and central sleep apnea (CSA). Although they are caused by different physiological phenomena, they are both associated with reductions (hypopneas) or complete cessations (apneas) in airflow, leading to a decrease in blood oxygen saturation, and an eventual cortical arousal and associated burst in sympathetic activity with an accompanied increase in heart rate and blood pressure.

Repetitive apnea and hypopnea events interrupt sleep continuity and reduce sleep time, which partly explains one of the defining symptoms: excessive daytime sleepiness. Sleep apnea has been associated with an increased risk of cardiac and cerebrovascular diseases such as hypertension, heart failure, arrhythmias, myocardial ischemia and infarction, pulmonary arterial hypertension, renal disease, metabolic dysregulation, insulin resistance and lipid disorders, stroke, dementia and cognitive impairment in the elderly, and changes in cerebral blood flow and cerebral autoregulation.

OSA is the most common type of sleep apnea and is caused by a complete or partial obstruction of the upper airway. Normally during sleep, muscles in the tongue, mouth and pharynx relax slightly but not enough to obstruct the airway. In the case of OSA, the muscles are relaxed too much. The tongue presses against the back of the upper airway obstructing the airflow towards the lungs.

During an OSA event, the heart rate decreases and the blood oxygen saturation reduces. When the brain does not get sufficient oxygen, because of the resistance to airflow, the obstruction may lead to arousals where the subject will partially or fully wake up from a sleep state. Usually, the subject gasps for air to re-establish airflow before returning to a sleep state. This is a cyclic pattern, which usually repeats (up to 100 times) throughout the night. OSA episodes last typically between 20 s and 40 s.

Although less common than OSA, CSA is nonetheless a relevant sleep breathing disorder, more often seen in patients suffering from other comorbidities, such as heart failure and neurological conditions. CSA is characterized by a cessation of airflow and also respiratory effort (apnea), or a reduction in airflow and respiratory effort without clear evidence of partially obstructed breathing (hypopnea).

In order to quantify the severity of a sleep disordered breathing condition, an index comprising both CSA and OSA apneas and hypopneas is used. The apnea-hypopnea index (AHI) reflects the average number of apneas and/or hypopneas per hour of observed sleep. In adults, an $AHI \leq 5$ is considered to be normal. Mild apnea is characterized by an AHI between 5-15 events per hour, moderate apnea between 15-30 events per hour, and severe apnea is associated with an AHI value greater than 30 events per hour. Often people are not aware of the frequent awakenings during the night.

Regarding apnea prevalence, $AHI \leq 5$ in adults between 30-60 years is about 9% for females and 24% for males. Obesity is the strongest risk factor for apnea and is reflected by several parameters including body mass index, neck circumference, and waist-to-hip ratio. Other risk factors include aging, gender, loss of muscle tone in pharynx, swollen tonsils, menopause, upper airway anatomy, smoking cigarettes, alcohol, ethnicity and the presence of other cardiac or neurological conditions. There seems to be a direct relationship between the apnea epidemic and the obesity epidemic.

There are many signs associated with apnea such as loud snoring, frequent awakenings from sleep gasping for air to restore airflow, or having a feeling of choking. People having apnea predominantly experience excessive daytime sleepiness or fatigue. Other complaints are related to insomnia and depressions. Fragmented sleep due to apnea may cause a poorer daytime cognitive performance, increased risk vehicle and workplace accidents.

Sleep apnea can be treated by applying continuous positive airway pressure (CPAP) through the nose by means of a mask that the patient has to wear during the night. The traditional practice of diagnosing sleep apnea is that patients are monitored during a sleep study. Sleep studies are expensive and require overnight polysomnography (PSG) evaluation in sleep laboratories as well as attending personal. A polysomnogram will typically record multiple parameters including:
  Electroencephalogram (EEG) for monitoring brain activity;
  Electrooculogram (EOG) to monitor eye movement;
  Electromyogram (EMG) to monitor muscle tension;
  Electrocardiogram (ECG) to monitor the electric activity of the heart;
  Respiratory inductance plethysmography or piezoelectric belts around the thorax and abdomen to measure respiratory effort;
  Nasal and oral thermistors or pressure sensors to measure airflow; and
  Pulse oximetry to monitor changes in blood oxygen levels.

Because of the limited availability of sleep laboratories and the high costs associated with sleep studies, under-diagnosis of sleep apnea is a large problem. It is reported that about 80%-85% of the people with OSA are under-diagnosed.

Various algorithms have been proposed for automatic sleep apnea screening. However, there exist about 80 different sleep disorders. Therefore, detecting sleep apnea in patients having sleep disorders is considered to be challenging. There are known algorithms to detect apnea and hypopnea episodes based on heart rate variability (HRV) features extracted from an ECG signal. An apnea/hypopnea episode has a significant impact on the instantaneous heart rate and hemodynamics. These episodes result in a recurring heart rate pattern, called cyclic variation of heart rate (CVHR). CVHR peaks are due to abrupt increases in heart rate during the arousal phase that terminates the apnea or hypopnea event.

It is widely recognized that undiagnosed sleep apnea is an important risk factor for the development of cardiovascular diseases (e.g. hypertension, stroke, and congestive heart failure), impairments in thinking and diabetes. Therefore, early and simplified diagnoses of sleep apnea using a limited number of sensor sources is desirable.

SUMMARY OF THE INVENTION

The invention is defined by the claims.

According to examples in accordance with an aspect of the invention, there is provided a system for detecting sleep apnea, comprising:
a physiological sensor for generating a sensor signal for use in detecting sleep apnea;
a processor, which is adapted to:
determine a first characteristic which depends on the physiological condition of a subject during sleep, in particular a sleep stage, or receive as input an identification of said first characteristic; and
detect an apnea event based on the sensor signal using a detection algorithm which is selected from a set of detection algorithms in dependence on the first characteristic.

This system is able to provide automatic sleep apnea screening based on features extracted from a physiological signal, for example as captured by a PPG sensor and/or an ECG sensor. The analysis of these features takes account of the a first characteristic which depends on the physiological condition of a subject during sleep at that time. The extracted features for example include information relating to heart rate variability (HRV).

In this way, an intermediate characteristic is obtained and is used to make a selection between a set of sleep apnea determination algorithms. Thus, there are at least two sleep apnea determination algorithms for at least two non-awake sleep states. This provides a two-stage detection process, whereby the physiological condition of a subject is first categorized, and that categorization helps to make a more accurate determination of an apnea event.

The first characteristic, namely the sleep stage, may be input to the system, for example from manual inspection of signals. However, the first characteristic detection is preferably automatic. For example, the processor may be adapted to determine a sleep stage from heart rate variability information derived from the sensor signal. The sleep stage is for example determined by a sleep stage classifier.

Automatic sleep stage detection has seen a substantial development and improvement in recent years based on heart rate variability (HRV) features extracted from an ECG signal or even a PPG signal. The same physiological sensor which enables sleep stages to be automatically identified may be used in the system of the invention to enable apnea events to be detected.

The invention enables higher detection accuracy compared to the known approaches to detect apnea and hypopnea events on the basis of HRV features extracted from a physiological signal. In particular, information which is dependent on the physiological condition of a subject during sleep, such as sleep-stage-specific information, is exploited in the process of apnea detection. Known solutions instead provide a generic classification scheme which is trained to find the mapping between apnea features extracted from a physiological signal, without taking account of sleep stage information or any other intermediate characteristic, which can also be extracted from the physiological signal.

The invention is for example based on training a sleep-stage-specific classifier, in an offline training stage, based on features extracted from a physiological signal that maximize apnea class separation within the various sleep stages.

In order to detect an apnea event in an instance (i.e. time frame) of a physiological signal, first the sleep stage associated to the instance may be estimated. Subsequently, apnea detection is based on applying a sleep-stage-specific apnea classifier.

The processor is for example adapted to:
extract heart beat timings from the sensor signal;
derive an interbeat interval time series; and
extract heart rate variability information from the interbeat interval time series.

It is known that heart rate variability information may be used as part of an automated apnea detection algorithm and also that heart rate variability may be used for sleep stage detection. The invention enables the same information source to be optimized for both types of detection to improve the accuracy of the apnea detection.

The processor is for example adapted to:
sample the sensor signal as a sequence of time frames;
extract first features of the sensor signal from each time frame; and
determine a sleep stage for each time frame from the first features.

Thus, the automatic sleep stage detection is carried out based on sequential time windows.

As mentioned above, the first features for sleep stage detection may comprise heart rate variability information.

The processor is for example further adapted to:
for each time frame, select an apnea classification model to be used for identifying sleep apnea from the sensor signal, the selection being in dependence on the previously determined sleep stage;
extract second features of the sensor signal from each time frame; and
determine an apnea or non-apnea state from the second features and from the selected apnea classification model.

The apnea detection is carried out using a model which depends on the sleep stage. The second features may also be extracted using a model which depends on the previously identified sleep stage.

Thus, the second features (for apnea detection) may be different to the first features (for sleep stage detection) and furthermore the second features may be chosen in dependence on the previously identified sleep stage. Thus, features which are most suitable for detecting apnea within a particular sleep stage are extracted, and they are then input to a suitable apnea classification model.

As mentioned above, the second features for apnea detection may also comprise heart rate variability information.

The invention also provides a method for detecting sleep apnea, comprising:
generating a sensor signal for use in detecting sleep apnea;
determining a first characteristic which depends on the physiological condition of a subject during sleep or receiving as input an identification of said first characteristic; and
detecting an apnea event based on the sensor signal by selecting a detection algorithm from a set of detection algorithms in dependence on the first characteristic.

The first characteristic is for example the sleep stage and the method may comprise determining a sleep stage from heart rate variability information derived from the sensor signal.

The method may comprise:
extracting heart beat timings from the sensor signal;
deriving an interbeat interval time series; and
extracting heart rate variability information from the interbeat interval time series.

This heart rate variability may be used both for sleep stage detection and for apnea detection.

The sleep stage detection part of the method may comprise:
sampling the sensor signal as a sequence of time frames;
extracting first features of the sensor signal from each time frame; and
determining a sleep stage for each time frame from the first features.

The apnea detection part of the method may comprise:
for each time frame, selecting an apnea classification model to be used for identifying sleep apnea from the sensor signal;
extracting second features of the sensor signal from each time frame using a model which depends on the previously identified sleep stage; and
determining an apnea or non-apnea state from the second features and from the selected apnea classification model.

The invention may be implemented at least in part in software.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
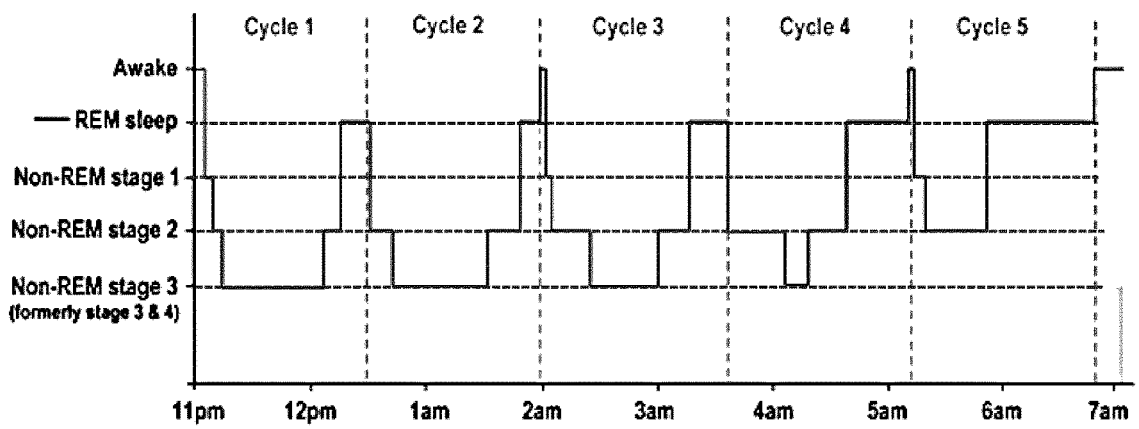
FIG. 1 shows a typical hypnogram indicating various sleep stages and cycles in adult sleep, in which the stages are represented as a function of time.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method and system for detecting sleep apnea, in which an intermediate characteristic, in particular a sleep stage, is determined, and an apnea event is detected based on a physiological sensor signal using a detection algorithm which is dependent on the determined sleep stage. By taking account of an intermediate characteristics such as the sleep stage when performing an automated apnea detection process, the accuracy of the apnea detection is improved.

FIG. 1 shows a typical hypnogram indicating various sleep stages and cycles in adult sleep, in which the stages are represented as a function of time. This is reproduced from https://www.howsleepworks.com/types_cycles.html.

Throughout the night, sleep progresses in healthy adults as a series of sleep cycles of non-REM and REM sleep. A sleep cycle has an average duration of approximately 90 minutes. Each sleep cycle follows multiple stages of non-REM sleep (categorized as stages N1, N2 and N3). After a period of sleep stage N3, the stages may progress back through N1 either to a period of waking, or a short period of REM sleep before returning to the progression N1 to N3 in a new sleep cycle. Usually, the time spent in sleep stage N3 decreases as the night progresses and the duration of REM sleep increases.

The sleep stages shown in FIG. 1 are defined by the American Academy of Sleep Medicine (AASM):

N1: Typically the first stage of sleep usually lasting between 1 and 5 minutes. It involves the transition period from an awake state to sleep. Brain waves emitted by the brain slow down.

N2: Characterized by a reduction in heart rate and decrease of core body temperature. There is a decrease in muscle activity. This stage contributes about 50% of the sleep period.

N3: Also known as deep sleep or slow wave sleep, due to the typical low frequency waves visible in a EEG recording. In this stage, the brain waves are least comparable to the awake state. There is a further decrease in muscle activity. It is difficult to wake a sleeper who is in deep sleep.

REM: Characterized by rapid eye movements. There is an occurrence of high frequency waves. The brain waves are most comparable to an awake state although most muscles are paralyzed during this stage.

People with sleep apnea have reduced N3 and REM duration as their sleep is fragmented by the arousals caused due to interrupted breathing. Typically, the sleep stages oscillate between W (Awake) and N1.

As mentioned above, automatic sleep stage detection has seen a substantial development and improvement in recent years based on heart rate variability (HRV) features extracted from an ECG signal or a PPG signal. For example, reference is made to:

[1] Berry, Richard B. et al. "Rules for Scoring Respiratory Events in Sleep: Update of the 2007 AASM Manual for the Scoring of Sleep and Associated Events: Deliberations of the Sleep Apnea Definitions Task Force of the American Academy of Sleep Medicine." Journal of Clinical Sleep Medicine: JCSM: Official Publication of the American Academy of Sleep Medicine 8.5 (2012): 597-619; and

[2] Fonseca P, Long X, Radha M, Haakma R, Aarts R M, Rolink J. "Sleep stage classification with ECG and respiratory effort", IOP Physiol Meas. 2015; 36:2027-2040.

This invention makes use of a physiological sensor to provide automatic detection of apnea events. The detection algorithm takes account of the sleep stage. The sleep stage may be manually input to the apnea detection algorithm, but in a preferred example the sleep stage detection is also automated. Furthermore, the sleep stages can be automatically identified with the same sensor modalities used for the apnea detection.

Figure 2:
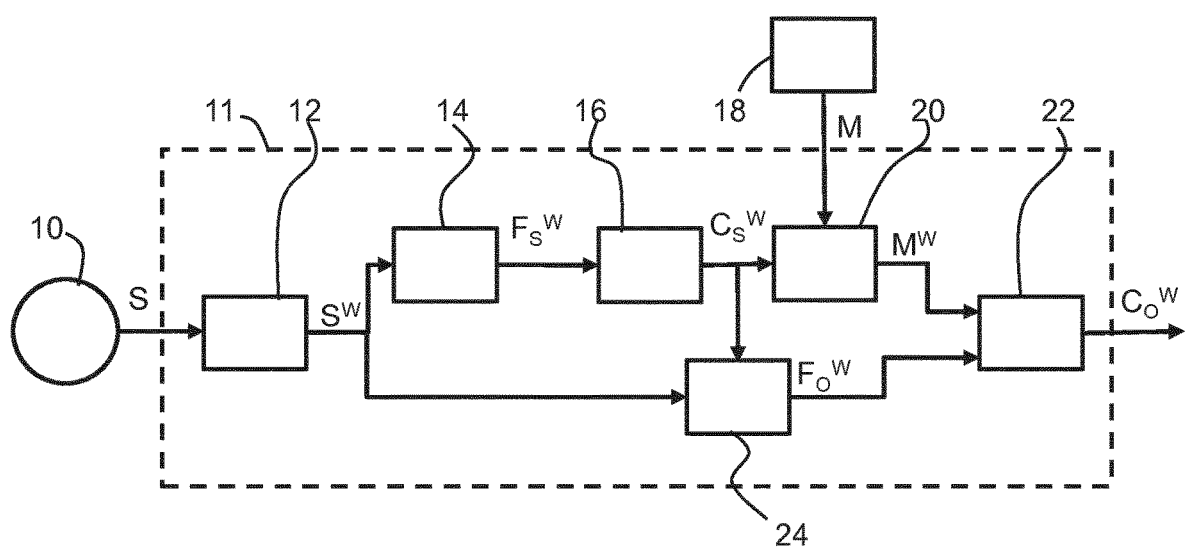
FIG. 2 shows a system in accordance with an example of the invention.

FIG. 2 shows a system in accordance with an example of the invention.

The system comprises a physiological sensor 10 which captures a sensor signal S from the human body. The signal is one which enables heart rate variability to be obtained. For this purpose, the sensor 10 may comprise a PPG sensor or an ECG sensor. Both sensing modalities may be used in combination to provide more robust heart rate monitoring information.

The sensor signal is provided to a processor 11, and the signal processing functions performed by the processor are explained below.

The raw sensor signal S is processed in epochs by a sampling unit 12 which samples the sensor signal as a sequence of time frames. The $w^{th}$ time frame in the sensor signal S is denoted by $S^W$.

A first feature extraction unit 14 is used for sleep stage detection. For a given time frame w, features $F_S^W$ are extracted from the time frames of the windowed sensor signal $S^W$ in order to assign a sleep stage to that time frame w. This is a first feature set. The time frames have a duration of the order of minutes, such as 2 to 10 minutes, and the time frames may overlap to define a shifting time window.

The feature set $F_S^W$ is input to a sleep stage detection unit 16. The feature extraction unit 14 may include additional pre/post-processing steps such as data cleaning, feature normalization and transformation.

The sleep stage detection unit 16 selects a sleep stage from a set $C_S$ which contains labels for all possible sleep stages, for example defined by: $C_S=\{W,N1,N2,N3,R\}$. W is the awake state, and the other sleep stages are outlined above. As explained further below, each state is the associated with a different apnea model for detecting an apnea event within each particular sleep stage.

A different set of sleep stages may instead be used, for example with more or fewer non-REM stages defined.

For example, the set may be defined as $Cs=\{W, N1$ and N2 combined, N3, REM$\}$. In practice it is difficult to separate N1 and N2 based only on HRV characteristics, so in a system which implements a sleep stage classifier to determine which apnea model to use, this would be a likely combination of stages.

A further simplified set may be defined as $Cs=\{W, $ non-REM, REM$\}$. The biggest differences, in terms of HRV characteristics during sleep, will be in these terms.

Alternatively, the set Cs could comprise clusters defining coherent HRV characteristics without necessarily being mapped to actual sleep stages. An apnea model could then be linked directly to each cluster, and the identification of the actual sleep stage is not needed. This approach also avoids the problem that the mapping between sleep stages and HRV is not completely unambiguous, due to the differences between central nervous system activity (CNS, where sleep is regulated) and autonomic nervous system activity (ANS, reflected by HRV). By trying to map from HRV characteristics to sleep stages to sleep apnea model, the best possible model may not result. By mapping directly from HRV to sleep apnea model, differences between CNS and ANS may be avoided.

In the following description, it is assumed that there is sleep stage identification.

A sleep stage classifier within the sleep stage detection unit 16 assigns a sleep stage class $C_S^W$ within set $C_S$ to the time frame w on the basis of the feature set $F_S^W$ that is provided to the input. The classifier for sleep stage detection is trained offline.

A set 18 of pre-trained classifiers for use in detecting sleep apnea are provided in a memory. The set M of sleep-stage-specific apnea classifiers is defined by $M=\{M_W, M_{N1}, M_{N2}, M_{N3}, M_R\}$. Each member of this set comprises one or more sensor signal characteristics which can be used to identify an apnea event within that particular sleep stage. Note that the classifier $M_W$ may simply comprise the indication that during wake periods, no apnea events can possibly occur, since these occur exclusively during sleep periods. There are at least two further sleep-stage-specific apnea classifiers in the set M.

Based on the detected sleep stage $C_S^W$, an apnea classification model $M^W$ within set M is selected by an apnea classifier model selection unit 20.

The selected model is then used in an apnea detection unit 22.

The apnea classification models in the set M are trained offline.

In parallel with the processing of the first feature set $F_S^W$, a second feature set $F_O^W$ is extracted from the sensor signal $S^W$ for each time frame w specifically for apnea detection. This is performed by a second feature extraction unit 24.

The types of features that are extracted within the time frame for apnea detection may be fixed, but they may instead depend on the sleep stage class that has been assigned to the time frame w by the sleep stage detection unit 16. This is shown in FIG. 2, where the assigned sleep stage class $C_S^W$ is input to the second feature extraction unit 24.

The features which are to be extracted for a specific sleep stage class are determined during an offline training phase.

In the apnea detection unit 22 an output is generated which represents a binary detection or non-detection of apnea. Thus, there is a set CO with only two class members CO={'apnea', 'non-apnea'}. One of the set members is provided as output $C_O^W$ for each time window. The apnea detection unit 22 receives as input the features $F_O^W$ extracted for apnea detection and the sleep-stage-specific classification model $M^W$.

As mentioned above, the features extracted relate to heart rate variability information.

HRV features can be grouped into the following categories:
Time domain linear features;
Frequency band power features;
Non-linear features describing irregularity of the interbeat time interval (IBI) series;
Hilbert transform and Discrete Wavelet Transform features.

Different examples of these features may provide the best correlation with a sleep apnea event for different sleep stages. This correlation is determined during a general system training phase.

Thus, each classification model $M_W$, $M_{N1}$, $M_{N2}$, $M_{N3}$, $M_R$ is based on a different set of HRV features. The features $F_O^W$ are then those that enable the classification model to be applied.

The number of HRV features that are ultimately used in each classification model corresponding to a specific sleep stage can be specified in advance during an offline training stage. Also, the number of features (i.e. predictors) selected for classification can be automatically tuned, for example using an algorithm which determines which subset of the available features yields the best classification performance.

By way of example, the training phase involves applying all available HRV features (there are for example 155 such features) and applying a feature selection process with the goal to find a subset of features that maximizes the separation between sleep apnea classes within a particular sleep stage. This means that the amount of features that eventually will be used to detect the sleep apnea events may vary across the different sleep stages.

Depending on the type of classification model used to construct the sleep apnea classifier, a combination, weighted combination or other function of HRV features may be made. Some classifiers may be interpreted as a function that extracts some set of features from the input, and the class probability output by the function is based on a weighted combination of the selected features.

Furthermore, different examples of these features may provide a better correlation with sleep stage than with sleep apnea event. Thus, different features are selected in the two feature extraction units. Again, this correlation is determined during a general system training phase.

Different HRV information will for example be most suitable for reliable sleep stage detection (i.e. $F_S^W$) as for apnea detection (i.e. $F_O^W$).

Different HRV information is also relevant for apnea detection as between the different sleep stages.

Figure 3:
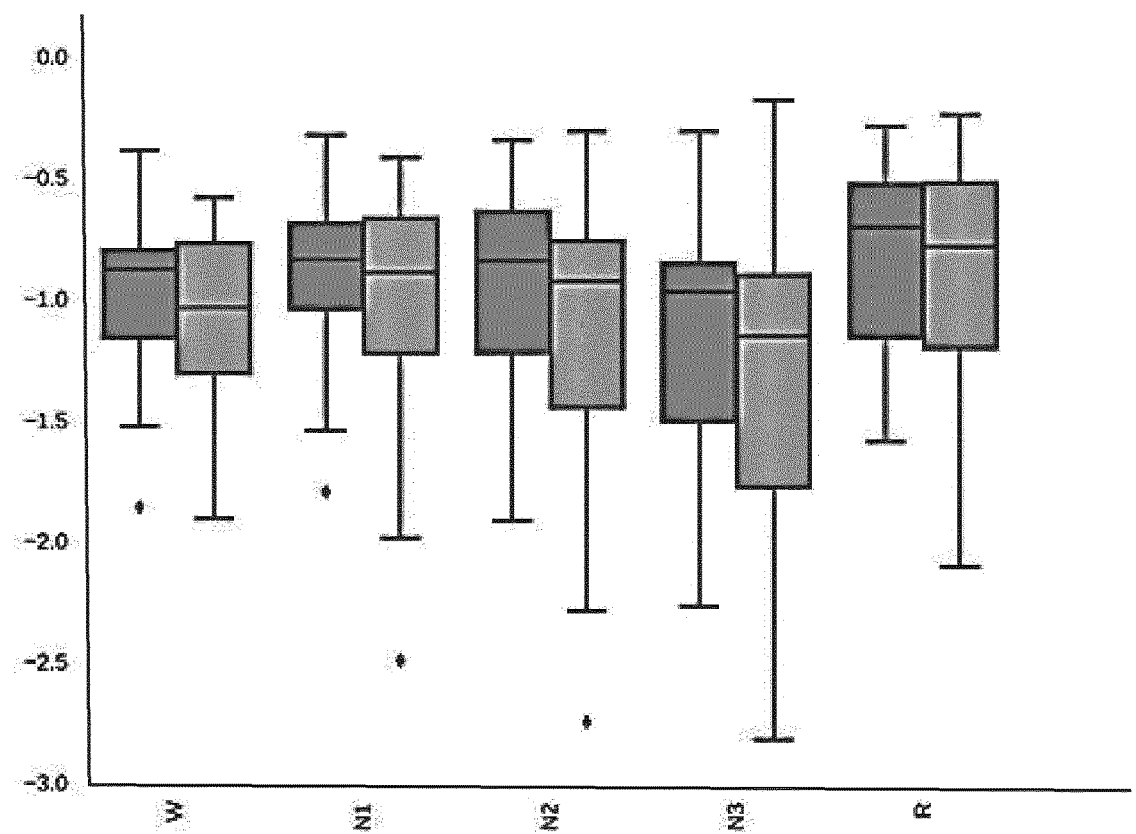
FIG. 3 shows how a particular heart rate feature varies for different sleep stages and at apnea and non-apnea times.

FIG. 3 shows the distribution of a specific HRV feature (power in the low frequency band, y-axis) across the different sleep stages (x-axis) for a dataset where all data samples were labelled as sleep apnea (the left bar of each pair) and non sleep apnea (the right bar of each pair). It shows that the feature distributions differ per sleep stage. This also demonstrates that applying a sleep stage specific sleep apnea classifier allows a greater class separation. As certain features contribute more or less to the predictive effect, the models ($M_W$ ... $M_R$, etc.) constructed to maximize the sleep apnea class separation within the respective sleep stage are likely to be different (i.e. contain different features as a result of the feature selection procedure, and may have different weights).

It is noted that different processing sub-units are shown in FIG. 2 to explain the underlying process. However, it will be apparent that all of these units in practice may be implemented by a single processor under the control of a suitable program. As can be seen, the input to the processor is the sensor signals and information about the classifiers M to be used for identifying apnea within different sleep stages. The processing tasks may however be split between multiple processors; some may be local to the sensor and others may be remote.

The sleep stages may be manually scored by system operators, on the basis of the visual analysis of PSG, EEG, EOG and EMG signals following established rules, e.g. following the manual of the American Academy of Sleep Medicine (AASM). In this case, sleep stage is input to the processor rather that the processor performing automated sleep stage detection. In such an embodiment, the feature extraction unit 14 for sleep stage detection and the sleep stage detection processing block 16 are replaced by a sleep stage input from this manual classification process.

Figure 4:
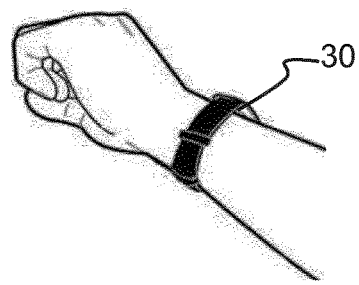
FIG. 4 shows the system as a wrist-worn sensor which is worn throughout the night.
Figure 4:
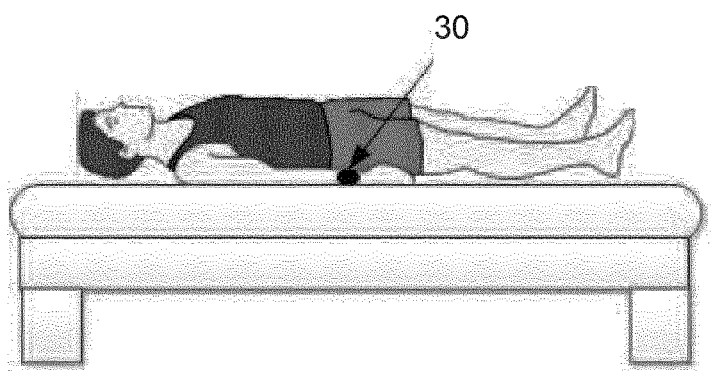

The system is preferably implemented as a wearable sensor which may be worn during sleep. FIG. 4 shows the system 30 as a wrist-worn sensor (as seen in the top image) which is worn throughout the night (as represented in the bottom image).

The wearable device comprises the sensor 10 that captures a physiological signal 10 and the, or part of the, processing unit 11. Some or all of the processing may be carried out locally at the worn system, and some or all may be carried at a back end system with which the worn system communicates over a wireless communications channel.

In a preferred embodiment, a photoplethysmography (PPG) sensor is used.

A PPG sensor is a pulse oximeter. While the purpose of such a sensor is to obtain a measure of blood oxygen saturation, it also detects changes in blood volume in the skin, and thereby performs PPG sensing. By detecting changes in blood volume, a cyclic signal corresponding to the pulse is obtained. PPG sensors, such as pulse oximeters, are thus commonly used to provide a measure of the pulse rate.

A PPG sensor contains at least one LED, and one light sensor. The LED and sensor are placed such that the LED directs light into the skin of the user, which is reflected or transmitted, and detected by the sensor. The amount of reflected/transmitted light is determined by, amongst others, the perfusion of blood within the skin.

The PPG system for example includes a red LED, a near-infrared LED, and a photodetector diode. The sensor is typically configured with the LEDs and photodetector diode directly on the skin of the subject.

The LEDs emit light at different wavelengths, which light is diffused through the vascular bed of the skin and received by the photodetector diode. The changing absorbance at each of the wavelengths is measured, allowing the sensor to determine the absorbance due to the pulsing arterial blood alone, excluding venous blood, skin, bone, muscle, and fat for example. The resulting PPG signal may then be analyzed.

Other simpler versions of a system for obtaining PPG data may be used, including a version with a single light source of one or more wavelengths. The absorption or reflectance of the light is modulated by the pulsatile arterial blood volume and detected using a photodetector device.

In transmissive pulse oximetry, a sensor device is placed on a thin part of the body of the subject. Reflectance pulse oximetry may be used as an alternative to transmissive pulse oximetry. This method does not require a thin section of the person's body and is therefore well suited to more universal application such as the wrist as shown above.

A basic design of a PPG sensor for example is a contact sensor with a single wavelength light source, e.g. green light (550 nm) to measure the PPG signal. The light source is pulsed with a certain light output frequency such as 128 Hz. A sampling frequency of the optical sensor is higher, for example 256 Hz so that it measures during light source activation and between light source activations. This allows the system to distinguish between the emitted light from the LED and the ambient light, and thereby filter out the ambient light from the signal received during a light source pulse.

In other known proposals, PPG data can be obtained from camera images, where ambient light and/or additional light sources are used to illuminate the tissue, such as skin. PPG measurements can thus even be carried out at a distance from the tissue, where the light source and/or detector are not in contact with the tissue, such as in the case of camera-based measurements.

The PPG data may be obtained at one or more wavelengths, such as any number of wavelengths typically between 1 and 10, but more than 10 wavelengths may even be used.

Apparatus and techniques for obtaining PPG data are well known in the art and indeed many different PPG sensors are commercially available. They are for example used in devices for measuring the heart rate during exercise.

As explained above, the features of interest of the PPG (or other) signal relate to the heart rate variability (HRV). For this purpose, the processing unit localizes in the PPG signal the beat onset of each cardiac cycle. There is then noise-robust estimation of the interbeat interval (IBI) time series. HRV features are then derived from the extracted IBI time series for the purpose of sleep stage detection and apnea detection.

As mentioned above, multiple sensors may be used to enable more robust determination of the features (such as HRV information) of interest. In addition, further sensors may be used such as an accelerometer, whose data can be used to identify and filter out information corrupted by movement artefacts, as well as to extract additional features that can be used to improve the sleep stage classification accuracy. Other sensors may be used to extract respiratory information. By way of example, characteristics derived from pulse oximetry ($SpO_2$) may be used, and these can be obtained from a multi-wavelength PPG sensor. These are features that describe the variation in oxygen saturation or desaturation in the blood, which also have a strong correlation with sleep apnea events.

Surrogate measures of respiratory effort can also be automatically derived from a raw PPG signal. In turn, these measures can be used to help separate types of apnea events, for example obstructive sleep apnea (in which there is an interruption in flow, but respiratory effort continues) versus central sleep apnea (in which respiratory effort also ceases). This could be implemented without adding an additional sensor, since it can be derived exclusively from PPG sensing.

Furthermore, other characteristics of a PPG signal may be interpreted, such as the features of the morphology of a PPG signal which correlate with sleep-stage-specific properties or apnea events.

Figure 5:
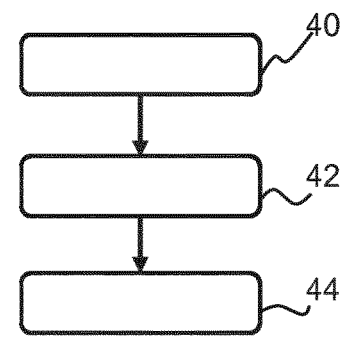
FIG. 5 shows the underlying method carried out by the system of FIG. 2.

FIG. 5 shows the underlying method carried out by the system of FIG. 2 for the instance where the sleep stage is determined or input to the system. The method comprises:

in step 40, generating a sensor signal for use in detecting sleep apnea;

in step 42, determining a sleep stage or receiving as input an identification of a sleep stage; and in step 44, detecting an apnea event based on the sensor signal using a detection algorithm which is dependent on the determined sleep stage.

The method may be generalized by considering the sleep stage to be a more generic first characteristic relating to physiological parameters of a subject during sleep.

The system of the invention has been tested by applying the processing to a dataset containing polysomnographic overnight recordings of subjects having sleep disordered breathing and sleep movement disorders.

As the physiological signal source, PPG data was used, with the sensor positioned on the subject's finger. Reference hypnograms from sleep sessions were obtained by expert review of sleep stages automatically classified by a sleep scoring system. Reference apnea and other sleep disorder events were scored with the same procedure.

The dataset contained 55 sleep sessions with a total duration of 10131 minutes, including 2876 minutes of annotated apnea events.

From the finger PPG, beat onset locations were derived and converted into an IBI time series. From the IBI time series, a total of 155 different HRV features were extracted.

The offline feature selection and model training process provides for each sleep stage a unique model that is based on a subset of features that maximizes the sleep apnea class separation for that sleep stage. These 155 features fall into the feature categories as described above.

Features were extracted from sliding windows (i.e. time frames) with a length of 270 seconds and overlap of 30 seconds.

Two experiments were performed to verify the hypothesis that applying a sleep-stage-specific apnea classifier allows a greater class separation compared to the use case where a non-sleep-stage-specific apnea detection model is applied. In order to estimate the accuracy of apnea detection in practice, a 10-fold cross validation was carried out by dividing the data into training/test splits so that receiver operating characteristics (ROCs) could be investigated.

In a first configuration A, an apnea prediction model that does not take sleep-stage-specific information into account was cross-validated. In other words, in each kth fold a generic classification model was trained that mapped the input feature space of the training set to the corresponding reference apnea event labels. As classifier, a logistic regression model was used. In the training phase a feature selection (Recursive Feature Elimination) was applied to each kth fold to enhance generalization by reducing overfitting. This is part of the model construction process.

From the features that were highest in rank, features that appear at least in six folds constitute the final feature set.

During the testing phase, the test data in each fold was split by the reference (ground truth) sleep stages assigned to the test epochs, and per sleep stage category the apnea detection performance was evaluated. More specifically, a ROC curve was constructed for each kth fold from the collection of apnea class probability estimates obtained by testing instances that originate from a specific sleep stage class.

In a second configuration B, the method explained above was evaluated. The training data was grouped by the reference sleep stage classes. Per sleep stage category, a dedicated apnea event detection model was trained in each kth fold. During training, the same logistic regression classification scheme and feature selection strategy were applied as was performed in configuration A.

In the testing phase, the focus was on studying the gain in apnea detection accuracy by applying a sleep-stage-specific apnea detection model. To test if an apnea event happened during a given epoch, the reference stage associated to the epoch was used to select the appropriate sleep-stage-specific apnea detection model. In other words, a hypothetically perfect sleep stage classifier was simulated instead of a sleep stage classifier that was trained with real feature data. Also in this case, for each kth fold, a ROC curve was constructed from the obtained apnea class probability estimates. This performance evaluation scenario is equivalent to splitting the test data by the reference sleep stages and evaluating per sleep stage category the apnea detection performance.

The results are shown as a plot of the 10-fold ROC signals, i.e. a plot of true positive rate versus false positive rate. The plots show lines for the 10 folds, the unity gradient line (dotted) and an average plot for all 10 folds (also dotted).

Figure 6:
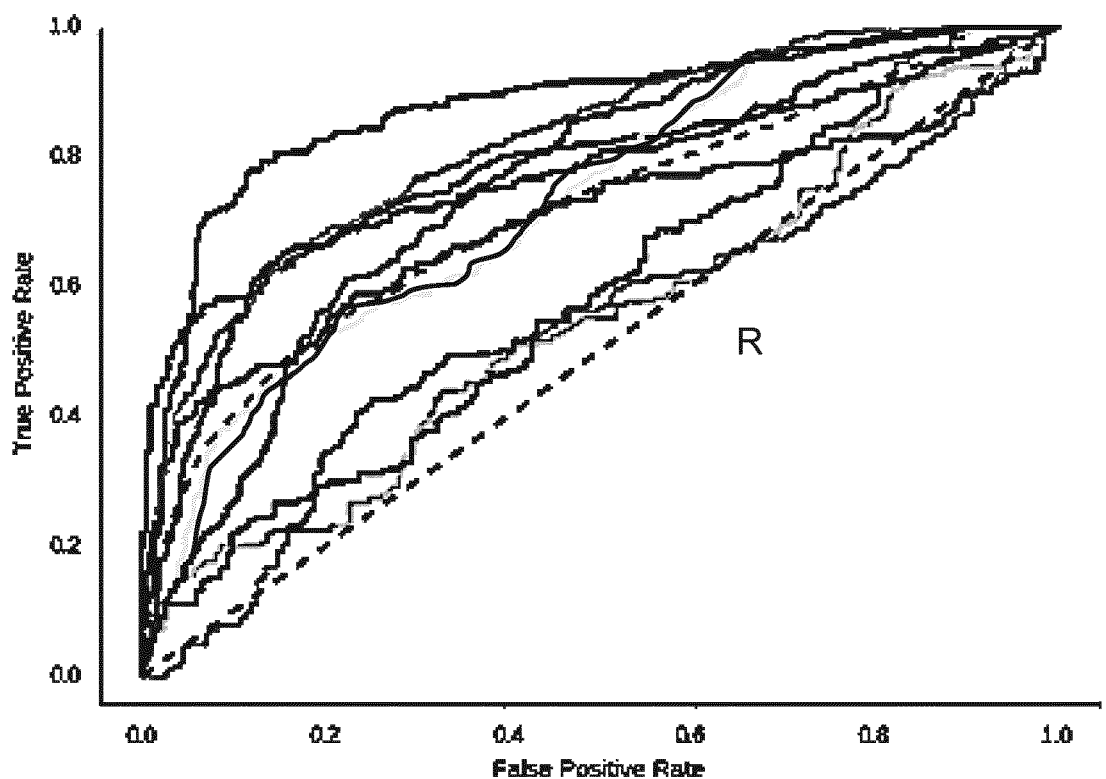
FIG. 6 shows the results of analysis of the performance of an apnea detection system which is independent of sleep stage for sleep stage R.
Figure 7:
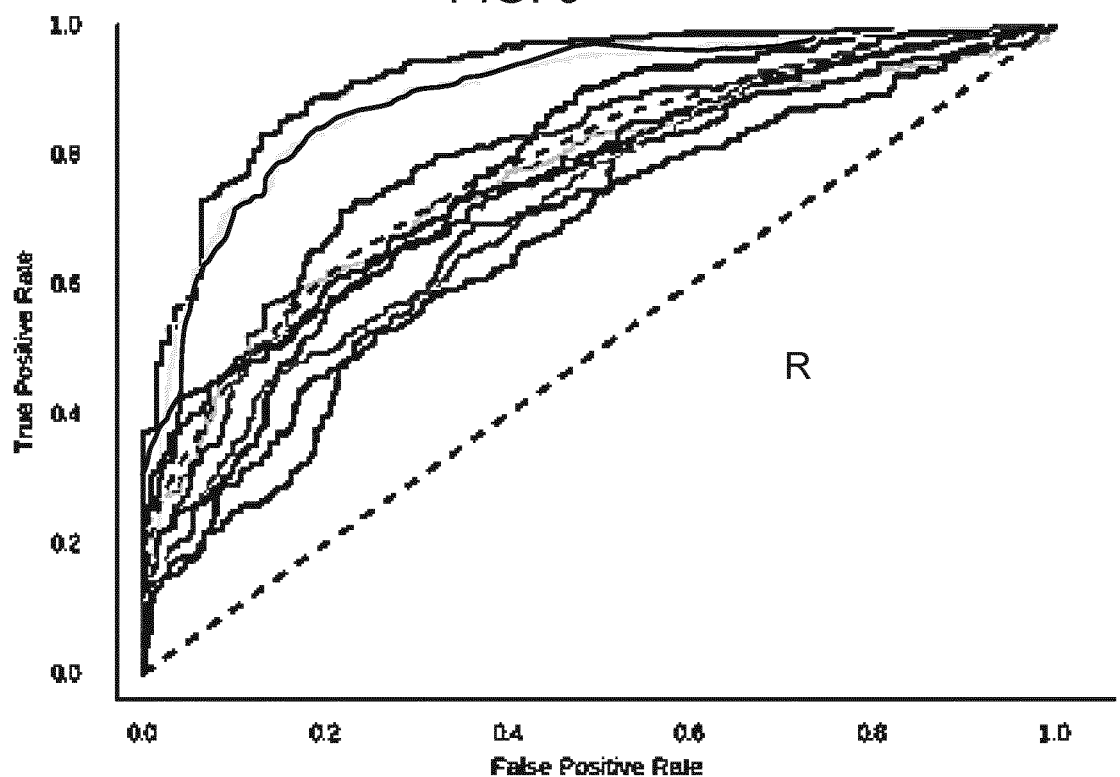
FIG. 7 shows the results of analysis of the performance of an apnea detection system in accordance with the invention for sleep stage R.

FIG. 6 shows the results of configuration A (the apnea detection independent of sleep stage) for the test set containing test instances (epochs) that originate from sleep stage R. FIG. 7 shows the corresponding results of configuration B (the apnea detection taking account of sleep stage), again for the sleep stage R.

Figure 8:
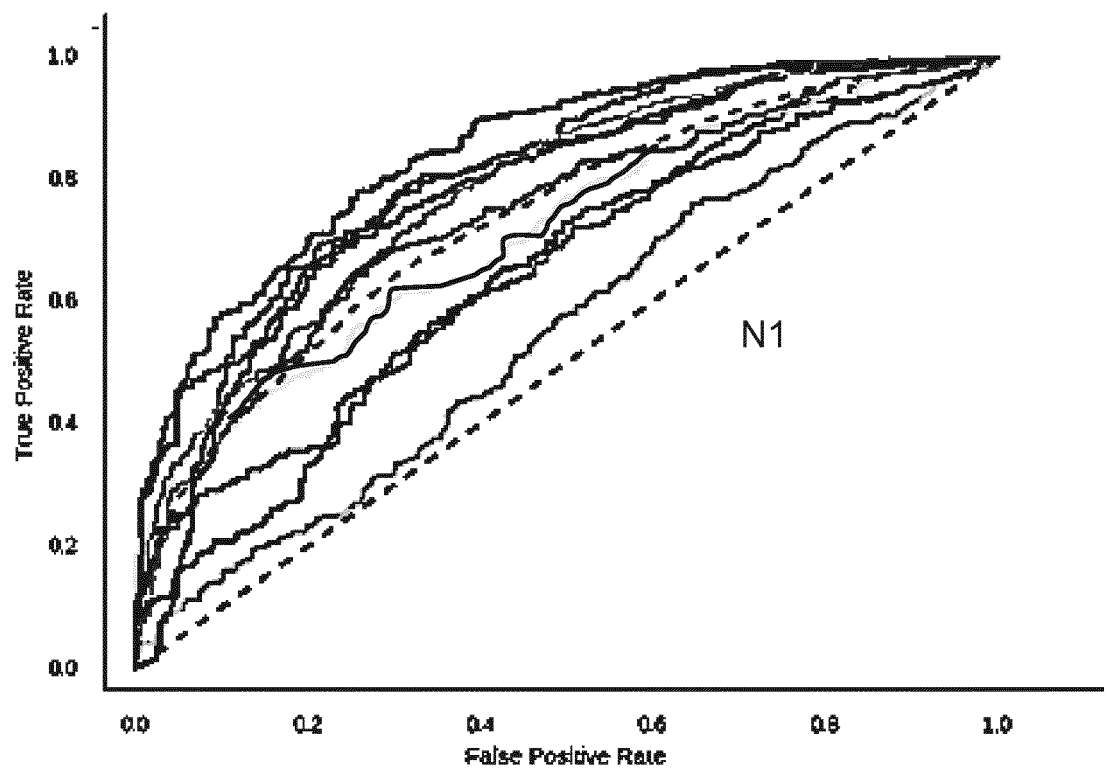
FIG. 8 shows the results of analysis of the performance of an apnea detection system which is independent of sleep stage for sleep stage N1.
Figure 9:
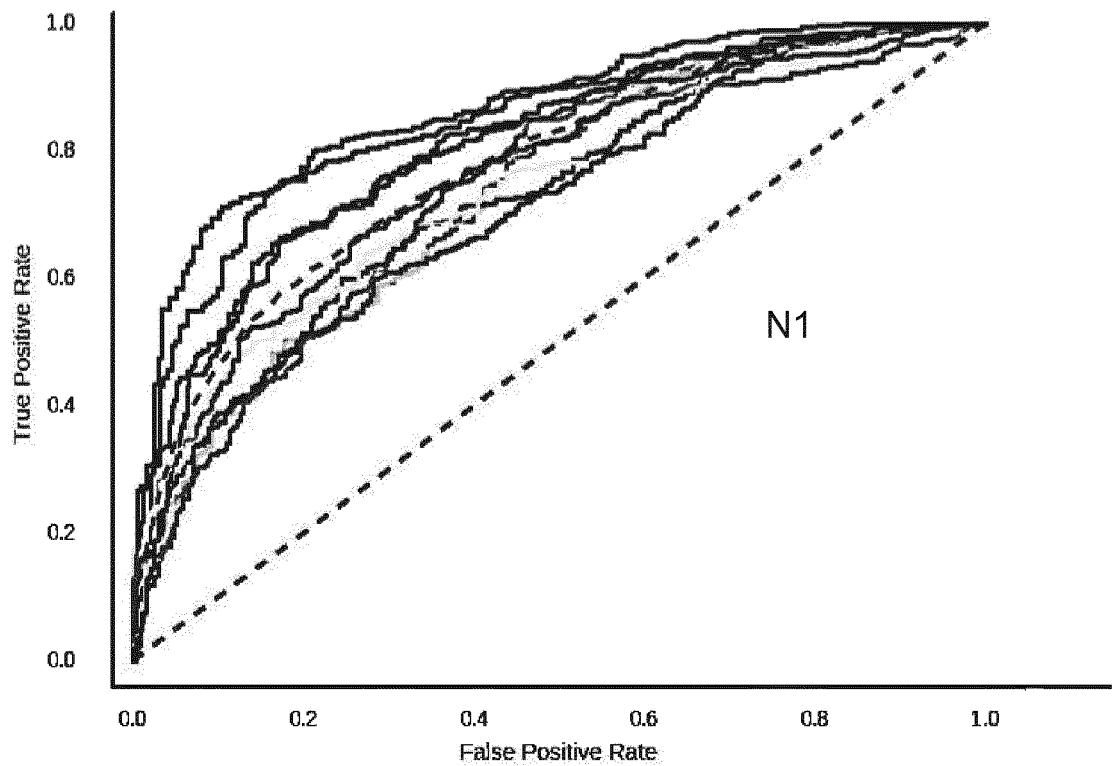
FIG. 9 shows the results of analysis of the performance of an apnea detection system in accordance with the invention for sleep stage N1.

FIG. 8 shows the results of configuration A (the apnea detection independent of sleep stage) for the test set containing test instances (epochs) that originate from sleep stage N1. FIG. 9 shows the corresponding results of configuration B (the apnea detection taking account of sleep stage), again for the sleep stage N1.

Figure 10:
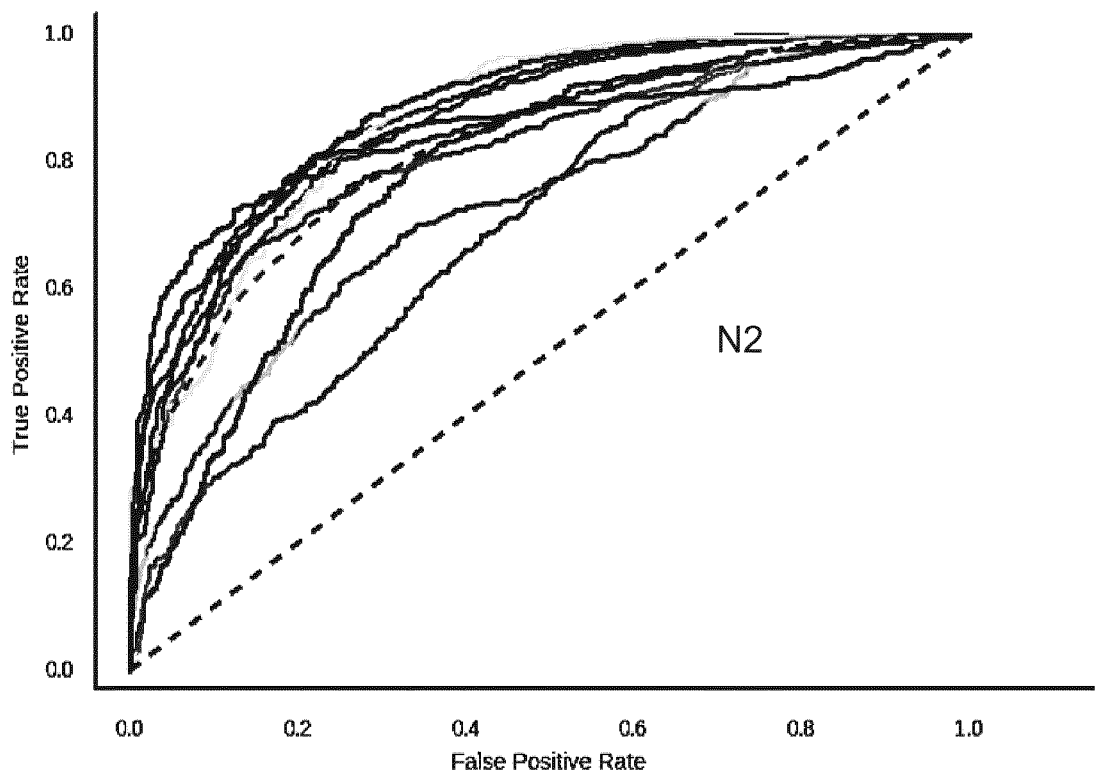
FIG. 10 shows the results of analysis of the performance of an apnea detection system which is independent of sleep stage for sleep stage N2.
Figure 11:
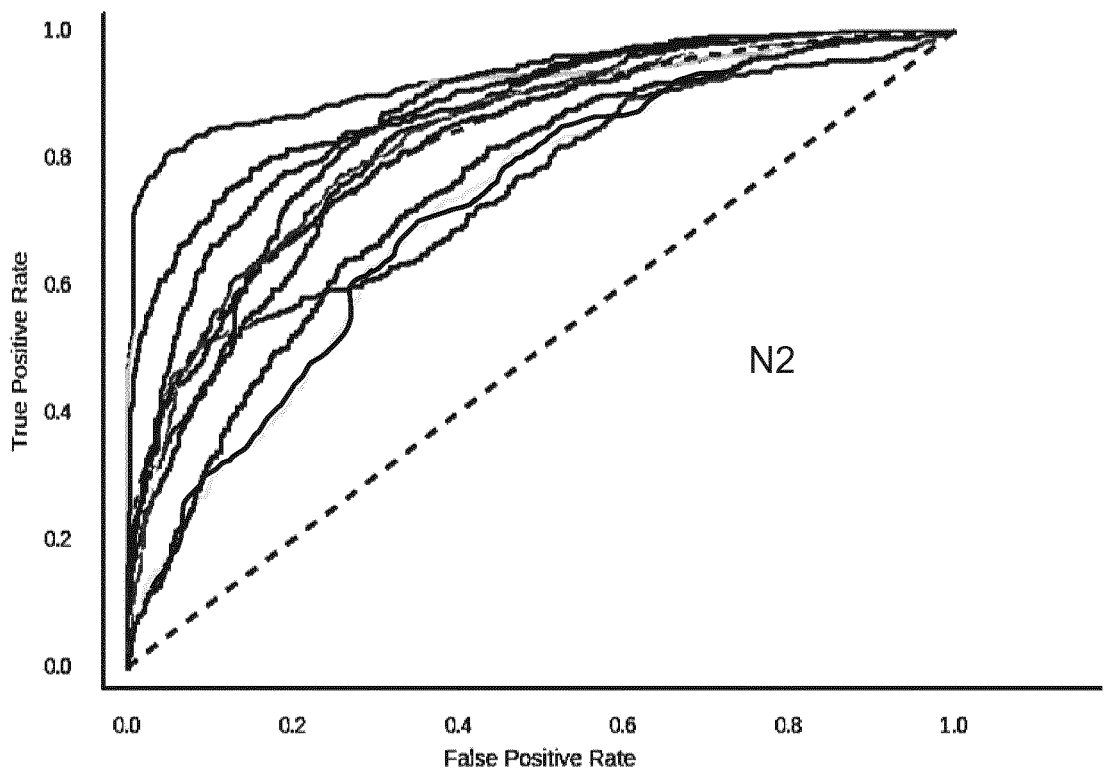
FIG. 11 shows the results of analysis of the performance of an apnea detection system in accordance with the invention for sleep stage N2.

FIG. 10 shows the results of configuration A (the apnea detection independent of sleep stage) for the test set containing test instances (epochs) that originate from sleep stage N2. FIG. 11 shows the corresponding results of configuration B (the apnea detection taking account of sleep stage), again for the sleep stage N2.

Figure 12:
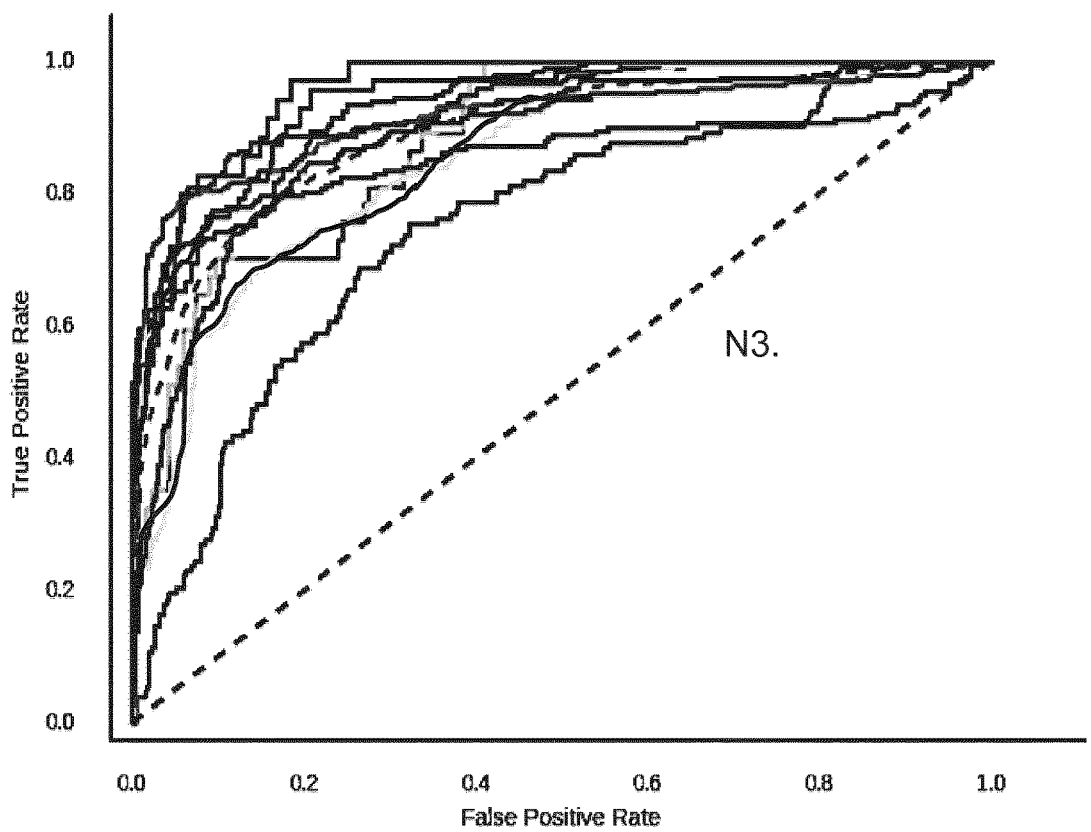
FIG. 12 shows the results of analysis of the performance of an apnea detection system which is independent of sleep stage for sleep stage N3.
Figure 13:
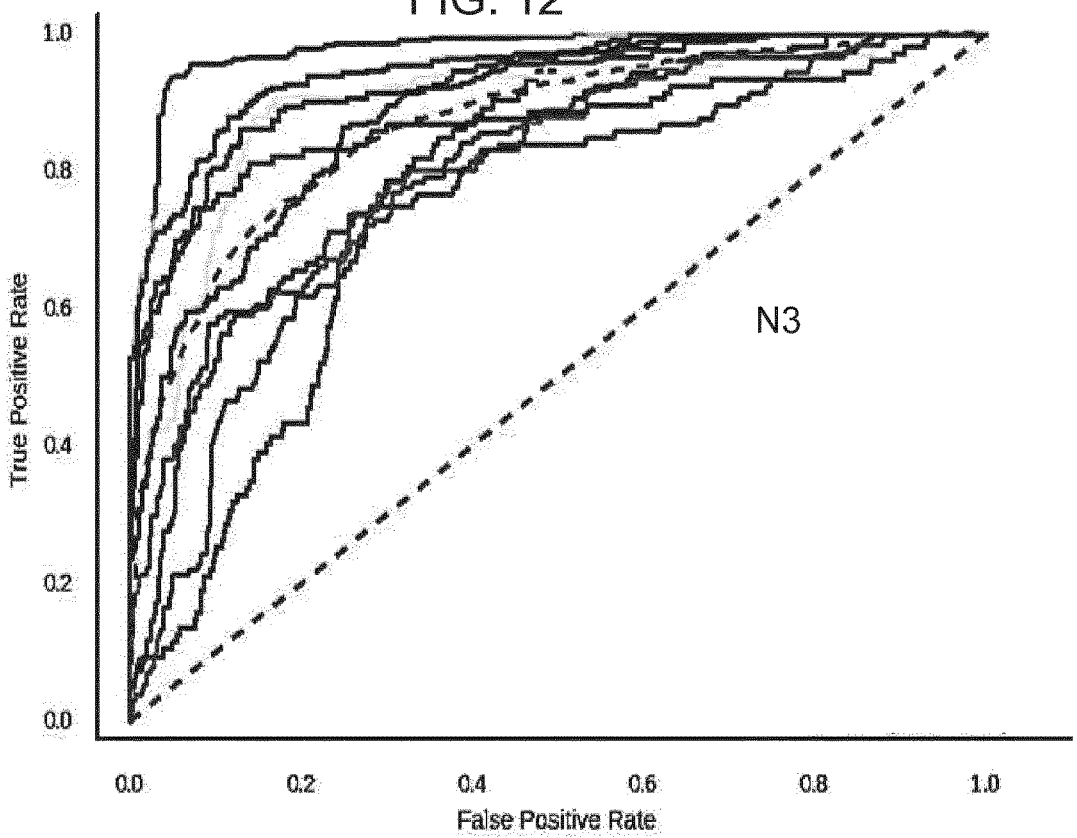
FIG. 13 shows the results of analysis of the performance of an apnea detection system in accordance with the invention for sleep stage N3.

FIG. 12 shows the results of configuration A (the apnea detection independent of sleep stage) for the test set containing test instances (epochs) that originate from sleep stage N3. FIG. 13 shows the corresponding results of configuration B (the apnea detection taking account of sleep stage), again for the sleep stage N3.

Figure 14:
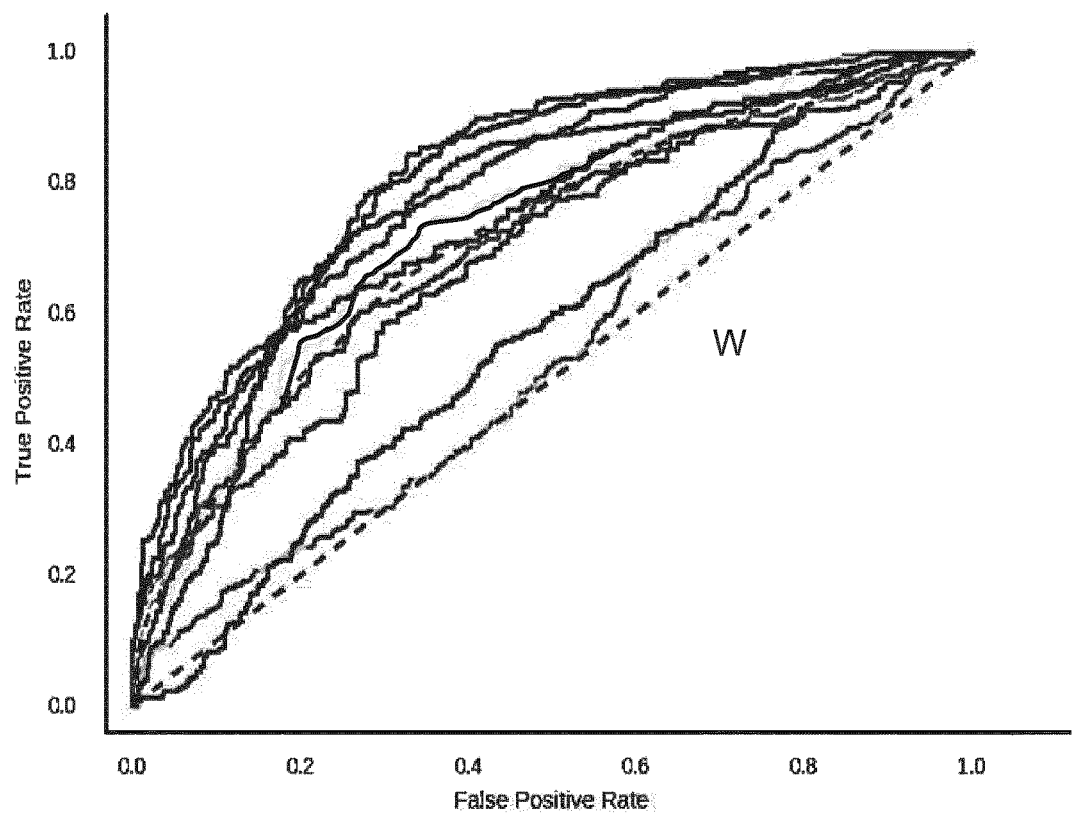
FIG. 14 shows the results of analysis of the performance of an apnea detection system which is independent of sleep stage for sleep stage W.
Figure 15:
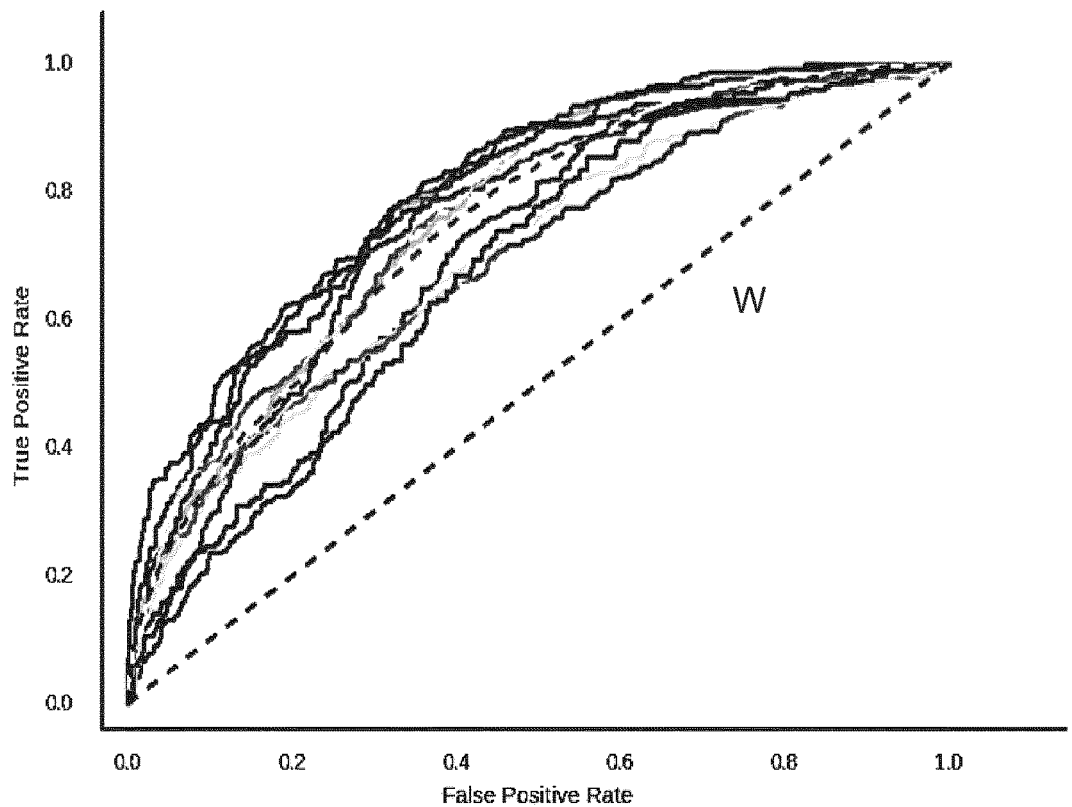
FIG. 15 shows the results of analysis of the performance of an apnea detection system in accordance with the invention for sleep stage W.

FIG. 14 shows the results of configuration A (the apnea detection independent of sleep stage) for the test set containing test instances (epochs) that originate from sleep stage W. FIG. 15 shows the corresponding results of configuration B (the apnea detection taking account of sleep stage), again for the sleep stage W.

Table 1 below provides an overview of the apnea prediction accuracy per sleep stage class measured by the mean area under the ROC curve (area under curve, AUC) that is constructed from the 10-fold cross-validation responses obtained in configurations A and B.

TABLE 1

| Sleep Stage | Config. A (AUC %) | Config. B (AUC %) |
| --- | --- | --- |
| W | 72 | 74 |
| N1 | 73 | 77 |
| N2 | 82 | 83 |
| N3 | 89 | 90 |
| R | 71 | 78 |

The results clearly indicate that applying a sleep-stage-specific apnea detection model outperforms the apnea event detection accuracy compared to a system in which a generic (non-sleep-stage-specific) apnea detection model is applied.

Across the tested sleep stages, ROC curves obtained in validating configuration B have, in general, a lower variation, and the curves in configuration A are in general closer to the diagonal of the ROC space which represents the random guess line. Moreover, the AUC values per evaluated sleep stage class obtained in configuration B are generally higher compared to results from configuration A.

In the example above, there is discrimination between apnea and non-apnea. The detection may be extended to distinguish between apnea and hypopnea, and between OSA and CSA, based on different resulting HRV patterns. For example, as mentioned above, other PPG characteristics, in particular those relating to surrogate measures of respiratory effort, could be used to distinguish OSA from CSA since the presence or absence of respiratory effort is the key factor distinguishing these two type of apnea event.

The detailed examples above relate to the identification of the sleep stage. However, as has been explained above, the invention relates more generally to any intermediate characteristic which then enables selection between multiple more tailored apnea detection algorithms. As mentioned above, there may be clusters or groups of coherent HRV characteristics, which can then each map to a separate algorithm for the apnea detection. This would avoid the need for actual sleep stage classification. The two-stage apnea detection approach would still provide improved accuracy in the apnea detection.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for detecting sleep apnea, comprising:
   a physiological sensor for generating a sensor signal from a user for use in detecting sleep apnea in the user; and
   a processor coupled to the physiological sensor, the processor being structured and configured to include:
   a sleep stage detection unit including a sleep stage classifier structured and configured to determine a sleep stage of the user based on heart rate variability information derived from the sensor signal;
   a plurality of pre-trained apnea classification models, each pre-trained sleep apnea classification model being associated with a particular one of a plurality of predetermined sleep stages and being structured and configured to automatically detect an apnea event based on the heart rate variability information, the plurality of predetermined sleep stages including at least two different non-awake sleep states;
   an apnea classification model selection unit structured and configured to select one of the pre-trained apnea classification models based on the determined sleep stage of the user; and
   an apnea detection unit structured and configured to determine whether apnea has been detected in the user using the selected one of the pre-trained apnea classification models and the heart rate variability information and to generate an output indicative of whether apnea has been detected.

2. The system as claimed in claim 1, wherein the physiological sensor comprises a PPG sensor and/or an ECG sensor.

3. The system as claimed in claim 1, wherein the processor is adapted to: extract heart beat timings from the sensor signal; derive an interbeat interval time series; and extract the heart rate variability information from the interbeat interval time series.

4. The system as claimed in claim 3, wherein the sleep stage classifier is structured and configured to: sample the sensor signal as a sequence of time frames; extract first features comprising the heart rate variability information from the sensor signal from each time frame; and determine the sleep stage for each time frame from the first features.

5. The system as claimed in claim 1, wherein the heart rate variability information is derived using a model which depends on a previously identified sleep stage.

6. A method for detecting sleep apnea, comprising:
   generating a sensor signal from a user for use in detecting sleep apnea using a physiological sensor;
   determining a sleep stage of a subject during sleep based on heart rate variability information derived from the sensor signal using a sleep stage classifier of a sleep stage detection unit implemented as part of a processor, wherein the processor includes a plurality of pre-trained apnea classification models, each pre-trained sleep apnea classification model being associated with a particular one of a plurality of predetermined sleep stages and being structured and configured to automatically detect an apnea event based on the heart rate variability information, the plurality of predetermined sleep stages including at least two different non-awake sleep states;
   selecting one of the pre-trained apnea classification models based on the determined sleep stage of the user using an apnea classification model selection unit implemented in the processor;
   determining, in an apnea detection unit implemented in the processor, whether apnea has been detected in the user using the selected one of the pre-trained apnea classification models and the heart rate variability information; and
   generating an output from the processor indicative of whether apnea has been detected.

7. The method as claimed in claim 6, comprising: extracting heart beat timings from the sensor signal; deriving an interbeat interval timeseries; and extracting the heart rate variability information from the interbeat interval time series.

8. The method as claimed in claim 7, comprising: sampling the sensor signal as a sequence of time frames; extracting first features comprising the heart rate variability information from of the sensor signal from each time frame; and determining a sleep stage for each time frame from the first features.

9. A computer program product, comprising a non-transitory computer usable medium having computer program code embodied therein which is adapted to implement the method for detecting sleep apnea as recited in claim 6.

* * * * *